(12) United States Patent
Backlund et al.

(10) Patent No.: US 12,076,394 B2
(45) Date of Patent: Sep. 3, 2024

(54) CYTOSOLIC DELIVERY OF PEPTIDES USING PROTEIN TRANSDUCTION DOMAIN MIMICS

(71) Applicant: University of Massachusetts, Boston, MA (US)

(72) Inventors: Coralie M. Backlund, Amherst, MA (US); Gregory N. Tew, South Deerfield, MA (US)

(73) Assignee: UNIVERSITY OF MASSACHUSETTS, Boston, MA (US)

( * ) Notice: Subject to any disclaimer, the term of this patent is extended or adjusted under 35 U.S.C. 154(b) by 305 days.

(21) Appl. No.: 17/321,168

(22) Filed: May 14, 2021

(65) Prior Publication Data

US 2021/0353746 A1 Nov. 18, 2021

Related U.S. Application Data

(60) Provisional application No. 63/025,210, filed on May 15, 2020.

(51) Int. Cl.

| | |
|---|---|
| *A61K 39/385* | (2006.01) |
| *A61K 39/00* | (2006.01) |
| *A61K 47/32* | (2006.01) |
| *C08F 234/02* | (2006.01) |
| *C08G 61/00* | (2006.01) |

(52) U.S. Cl.
CPC ............ *A61K 39/385* (2013.01); *A61K 47/32* (2013.01); *C08F 234/02* (2013.01); *A61K 2039/55561* (2013.01); *A61K 2039/6093* (2013.01); *C08G 61/00* (2013.01); *C08G 2261/126* (2013.01); *C08G 2261/1426* (2013.01); *C08G 2261/143* (2013.01)

(58) Field of Classification Search
CPC .................. A61K 39/385; A61K 47/32; A61K 2039/55561; A61K 2039/6093; A61K 47/59; A61K 47/58; A61K 39/39; A61K 2039/5154; C08F 234/02; C08G 61/00; C08G 2261/126; C08G 2261/1426; C08G 2261/143; C07K 14/77

See application file for complete search history.

(56) References Cited

U.S. PATENT DOCUMENTS

2016/0324970 A1* 11/2016 Tew ..................... G01N 33/588

OTHER PUBLICATIONS

Song TRL9 agonist enhances peptide Scientific Reports, Jul. 2015.*
Kamalov Siinfekl Hydrogel, Scientific Reports Feb. 2019.*

* cited by examiner

*Primary Examiner* — Sarah Alawadi
*Assistant Examiner* — Thurman Wheeler
(74) *Attorney, Agent, or Firm* — Milstein Zhang & Wu LLC

(57) ABSTRACT

The invention provides compositions and methods for cytosolic delivery of peptides and antigens as well as concomitant delivery of antigens and agonists via poly-norbornene-based protein transduction domain mimics.

10 Claims, 6 Drawing Sheets

CYTOSOLIC DELIVERY OF PEPTIDES USING PROTEIN TRANSDUCTION DOMAIN MIMICS

PRIORITY CLAIMS AND RELATED APPLICATIONS

This application claims the benefit of priority to U.S. Provisional Application No. 63/025,210, filed May 15, 2020, the entire content of which is incorporated herein by reference for all purposes.

TECHNICAL FIELD OF THE INVENTION

The invention generally relates to intracellular delivery of peptides. More particularly, the invention relates to compositions and methods for cytosolic delivery of peptides via poly-norbornene-based protein transduction domain mimics.

BACKGROUND OF THE INVENTION

Vaccines are currently one of the most effective means of preventing diseases. New vaccines are being sought to train the immune system as a therapeutic approach to treat diseases such as cancer. For protein-based vaccines, delivering the antigen into the cytosol has considerable challenges due to the impermeability of the cell membrane. A diversity of approaches has been explored for delivering antigens to optimally stimulate T cells that will mount an adaptive immune response. (Walker, et al. *Oncoimmunology* 2016, 5 (3), e1095435; Foster, et al. *Bioconjug. Chem.* 2010, 21 (12), 2205-2212; Krishnamachari, et al. *Pharm. Res.* 2011, 28 (2), 215-236; Irvine, et al. *Chemical Reviews.* 2015, pp 11109-11146; Kapadia, et al. *J. Control. Release* 2015, 219, 167-180.)

Designing an effective major histocompatibility complex (MHC) I vaccine is important for immunotherapies because it results in the training and expansion of cytotoxic lymphocytes (CTLs) against a very specific epitope. Targeted loading into MHC I is particularly attractive since it requires the antigen to be present in the cytosol for loading and display alongside costimulatory markers that promote an immune response. Advances in understanding antigen presentation by the innate immune cells and their interaction with the adaptive immune system have facilitated a rational approach for design and development of vaccine delivery systems. The key elements of an effective vaccine are the antigen, agonist, and a delivery system to facilitate the uptake of the cargos into the cytosol of antigen presenting cells (APCs) for presentation on MEW class I. (Butterfield *BMJ* 2015, 350 (5), h988; Nestle, et al. *Curr. Opin. Immunol.* 2005, 17 (2), 163-169; Amoozgar, et al. *Adv. Drug Deliv. Rev.* 2015, 91, 38-51; Sandev, et al. *Pharm. Res.* 2014, 31 (10), 2563-2582.)

Nanocarriers are well suited for vaccines because they provide encapsulation and protection, as well as deliver antigen and agonist for priming of CTLs. Recently, there has been a substantial increase in publications around immunization based on synthetic carriers, advancing the understanding of important design criteria to elicit a robust immune response with minimal toxicity. Many of these nanocarriers are able to exhibit a strong immune response both in vitro and in vivo, demonstrating their ability to prime CTLs against a specific antigen. (Sandev, et al. *Pharm. Res.* 2014, 31 (10), 2563-2582; Foster, et al. *Bioconjug. Chem.* 2010, 21 (12), 2205-2212; Molino, et al. *Biomaterials* 2016, 86, 83-91; Kwon, et al. *J. Control. Release* 2005, 105 (3), 199-212; Kapadia, et al. *Mol. Pharm.* 2016, 13 (10), 3381-3394; Molino, et al. *ACS Nano* 2013, 7 (11), 9743-9752.)

In addition to a variety of lipid and synthetic carriers, cell penetrating peptides (CPPs) have been studied for intracellular delivery in vaccine delivery systems. Commonly reported cell penetrating peptides include R9, a string of 9 arginines, and pep-1, an amphiphilic cell penetrating peptide reported to deliver cargo non-covalently. Previous reports of peptide delivery for vaccines use either chemical conjugation or a fusion construct with different types of antigen cargos, including protein, peptides, DNA, and siRNA. Apart from facilitating intracellular delivery, several examples of CPPs have been reported to prime antigen-specific CTLs. CPPs are attractive because they offer an all-inclusive delivery platform that has shown enhanced immune stimulation. (Walker, et al. *Oncoimmunology* 2016, 5 (3), e1095435; Jiang, et al. *Curr. Pharm. Biotechnol.* 2014, 15, 256-266; Apostolopoulos, et al. *Vaccine* 2006, 24, 3191-3202; Chikh, et al. *Eur. J Immunol.* 2003, 33 (4), 850-860; Mitsui, et al. *J. Invest. Dermatol.* 2006, 126, 1804-1812; Schutze-Redelmeier, et al. *Vaccine* 2004, 22 (15-16), 1985-1991; Kim, et al. *J. Immunol.* 1997, 159, 1666-1668; Lu, et al. *J. Immunol.* 2004, 172 (7), 4575-4582; Pouniotis, et al. *Immunology* 2006, 117 (3), 329-339; Derouazi, et al. *Cancer Res.* 2015, 75 (15), 3020-3031.)

Although straightforward, CPPs often require conjugation to their cargo. It was previously shown non-covalent delivery of functional cargos into the cytosol and nucleus of T cells using synthetic CPPs, also termed protein transduction domain mimics (PTDMs). Similar to CPPs, these amphiphilic polymers interact with cell membranes via guanidine moieties, while the hydrophobic block provides association with proteins. (Sgolastra, et al. *J. Control. Release* 2017, 254, 131-136; deRonde, et al. *Biomacromolecules* 2015, 16 (10), 3172-3179.)

There remains a significant unmet need for novel approaches, compositions and methods that achieve efficient and controlled cytosolic delivery of peptides.

SUMMARY OF THE INVENTION

The invention provides compositions and methods for efficient and controlled cytosolic delivery of peptides and antigens and antigen-agonist pairs. The strategy disclosed herein employs certain poly-norbornene-based PTDMs for a non-covalent delivery. Peptide delivery into, for example, monocytes in whole blood, is disclosed herein as a rapid process without being innately immunogenic even at increased concentrations lending the ability to tune activation (e.g., using the TLR9 agonist CpG as demonstrated herein). Additionally, the copolymer described here is superior at directing monocyte uptake of the non-covalently complexed cargo when compared with the CPP counterparts that inspired its design.

In one aspect, the invention generally relates to a complex of a peptide with one or more polymer molecules, wherein the peptide is non-covalently complexed to one or more molecules of a block copolymer having the Formula of (I):

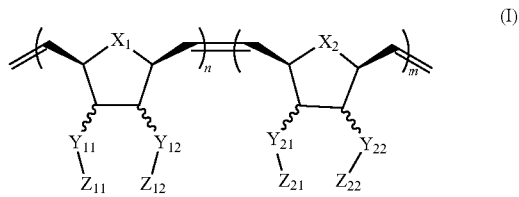

wherein
X₁, X₂ each is independently O or CH₂;
Y₁₁, Y₁₂ each is independently a single bond or a linking group;
Z₁₁, Z₁₂ each is independently

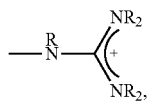

wherein each R is independently hydrogen or a $C_1$-$C_6$ (e.g., $C_1$, $C_2$, $C_3$, $C_4$, $C_5$, $C_6$) alkyl group;
Y₂₁, Y₂₂ each is independently a single bond or a linking group;
Z₂₁, Z₂₂ each is independently alkyl, substituted alkyl, aryl, or substituted aryl group;
and
m, n each is independently an integer from about 2 to about 50.

In another aspect, the invention generally relates to a composition comprising a complex disclosed herein.

In yet another aspect, the invention generally relates to a method for delivering a peptide to cytosol. The method comprises: providing a complex of the peptide with a block copolymer; and contacting the complex with a cell under conditions suitable for intracellular uptake of the complex, wherein the block copolymer has the Formula of (I):

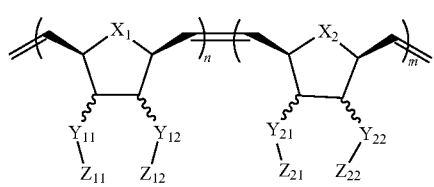

wherein
X₁, X₂ each is independently O or CH₂;
Y₁₁, Y₁₂ each is independently a single bond or a linking group;
Z₁₁, Z₁₂ each is independently

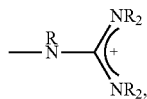

wherein each R is independently hydrogen or a $C_1$-$C_6$ (e.g., $C_1$, $C_2$, $C_3$, $C_4$, $C_5$, $C_6$) alkyl group;
Y₂₁, Y₂₂ each is independently a single bond or a linking group;
Z₂₁, Z₂₂ each is independently alkyl, substituted alkyl, aryl, or substituted aryl group; and
m, n each is independently an integer from about 2 to about 50.

In yet another aspect, the invention generally relates to a method for concomitant delivery of an antigen and an agonist to cytosol. The method comprises: providing a complex comprising the antigen and the agonist each non-covalently complexed to a block copolymer; and contacting the complex with a cell under conditions suitable for intracellular uptake of the complex, wherein the block copolymer has the Formula of (I):

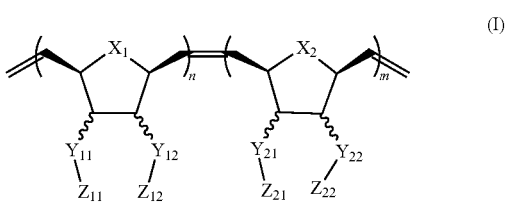

wherein
X₁, X₂ each is independently O or CH₂;
Y₁₁, Y₁₂ each is independently a single bond or a linking group;
Z₁₁, Z₁₂ each is independently

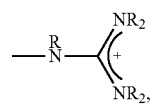

wherein each R is independently hydrogen or a $C_1$-$C_6$ alkyl group;
Y₂₁, Y₂₂ each is independently a single bond or a linking group;
Z₂₁, Z₂₂ each is independently alkyl, substituted alkyl, aryl, or substituted aryl group;
and
m, n each is independently an integer from about 2 to about 50.

DEFINITIONS

Figure 1:
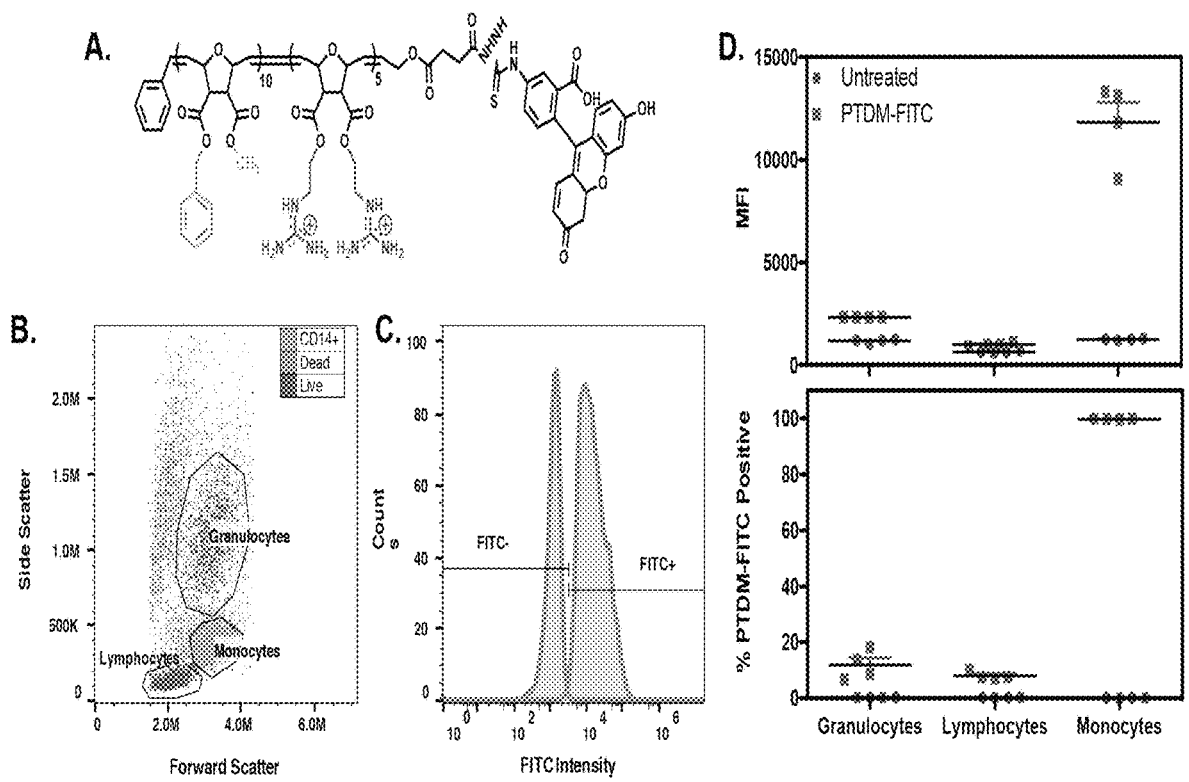
FIG. 1. Delivery of 2.8 μM fluorescein isothiocyanate (FITC) labeled PTDM (A) into whole blood for 1 hour. Cells were gated morphologically (B) and monocytes were confirmed with α-CD14 staining, while granulocytes were confirmed with α-CD15 staining within the respective morphological gate. Uptake within each of the morphological gates was determined by a shift in FITC intensity from the blank (C). The mean±SEM of the median fluorescence intensity (MFI) on the top and percent positive cells on the bottom of 4 separate donors is shown (D).

Unless defined otherwise, all technical and scientific terms used herein have the same meaning as commonly understood by one of ordinary skill in the art to which this invention belongs. General principles of organic chemistry, as well as specific functional moieties and reactivity, are described in "Organic Chemistry", Thomas Sorrell, University Science Books, Sausalito: 1999, and "March's Advanced Organic Chemistry", 5$^{th}$ Ed.: Smith, M. B. and March, J., John Wiley & Sons, New York: 2001, the entire contents of which are hereby incorporated by reference.

As used herein, the term "agonist" refers to a compound that, in combination with a receptor, can produce a cellular response. An agonist may be a ligand that directly binds to the receptor. Alternatively, an agonist may combine with a receptor indirectly by, for example, (a) forming a complex with another molecule that directly binds to the receptor, or (b) otherwise resulting in the modification of another compound so that the other compound directly binds to the receptor.

As used herein, the term "antigen" as used herein is meant any substance that causes the immune system to produce antibodies and/or specific cell-mediated immune responses against it. A disease associated antigen is any substance that is associated with any disease that causes the immune system to produce antibodies and/or a specific-cell mediated response against it. An antigen is capable of being recognized by the immune system and/or being capable of inducing a humoral immune response and/or cellular immune response leading to the activation of B- and/or T-lymphocytes. An antigen can have one or more epitopes (B-and/or T-cell epitopes). An antigen will preferably react, typically in a highly selective manner, with its corresponding antibody or TCR and not with the multitude of other antibodies or TCRs which may be evoked by other antigens. Antigens as used herein may also be mixtures of several individual antigens.

As used herein, the term "alkyl" refers to a straight, branched or cyclic hydrocarbon radical consisting solely of carbon and hydrogen atoms, containing no unsaturation, having from one to ten carbon atoms (e.g., C$_{1-10}$ alkyl). Whenever it appears herein, a numerical range such as "1 to 10" refers to each integer in the given range; e.g., "1 to 10 carbon atoms" means that the alkyl group can consist of 1 carbon atom, 2 carbon atoms, 3 carbon atoms, etc., up to and including 10 carbon atoms, although the present definition also covers the occurrence of the term "alkyl" where no numerical range is designated. In some embodiments, "alkyl" can be a C$_{1-6}$ alkyl group. In some embodiments, alkyl groups have 1 to 10, 1 to 8, 1 to 6, or 1 to 3 carbon atoms. Representative saturated straight chain alkyls include, but are not limited to, -methyl, -ethyl, -n-propyl, -n-butyl, -n-pentyl, and -n-hexyl; while saturated branched alkyls include, but are not limited to, -isopropyl, -sec-butyl, -isobutyl, -tert-butyl, -isopentyl, 2-methylbutyl, 3-methylbutyl, 2-methylpentyl, 3-methylpentyl, 4-methylpentyl, 2-methylhexyl, 3-methylhexyl, 4-methylhexyl, 5-methylhexyl, 2,3-dimethylbutyl, and the like. The alkyl is attached to the parent molecule by a single bond. Unless stated otherwise in the specification, an alkyl group is optionally substituted by one or more of substituents.

As used herein, the terms "aryl" or "aromatic" refer to a radical with 6 to 14 ring atoms (e.g., C$_{6-14}$ aromatic or C$_{6-14}$ aryl) that has at least one ring having a conjugated pi electron system which is carbocyclic (e.g., phenyl, fluorenyl, and naphthyl). In some embodiments, the aryl is a C$_{6-10}$ aryl group. For example, bivalent radicals formed from substituted benzene derivatives and having the free valences at ring atoms are named as substituted phenylene radicals. In other embodiments, bivalent radicals derived from univalent polycyclic hydrocarbon radicals whose names end in "-yl" by removal of one hydrogen atom from the carbon atom with the free valence are named by adding "-idene" to the name of the corresponding univalent radical, e.g., a naphthyl group with two points of attachment is termed naphthylidene. Whenever it appears herein, a numerical range such as "6 to 14 aryl" refers to each integer in the given range; e.g., "6 to 14 ring atoms" means that the aryl group can consist of 6 ring atoms, 7 ring atoms, etc., up to and including 14 ring atoms. The term includes monocyclic or fused-ring polycyclic (i.e., rings which share adjacent pairs of ring atoms) groups. Polycyclic aryl groups include bicycles, tricycles, tetracycles, and the like. Unless stated otherwise in the specification, an aryl moiety can be optionally substituted by one or more substituents.

As used herein, the terms "linking group" or "linker" refer to a spacer or functional group that covalently connects two or more groups, parts or fragments of a molecule.

As used herein, the term "peptide" refers to an oligomer or polymer of amino acid residues, and are not limited to a minimum length. Thus, peptides may be dimers, multimers, oligopeptides, or polypeptides. The terms also include post-expression modifications of the polypeptide, for example, glycosylation, acetylation, phosphorylation, and the like. Furthermore, a polypeptide may refer to a protein which includes modifications, such as deletions, additions, and substitutions (generally conservative in nature), to the native sequence, as long as the protein maintains the desired activity. These modifications may be deliberate or may be accidental.

Any compositions or methods disclosed herein can be combined with one or more of any of the other compositions and methods provided herein.

DETAILED DESCRIPTION OF THE INVENTION

The invention is based in part on the discovery of efficient and controlled cytosolic delivery of peptides via certain poly-norbornene-based PTDMs in a non-covalent delivery of antigens and antigen-agonist pairs.

As disclosed herein, a model peptide SIINFEKL was chosen for proof-of-concept studies. SIINFEKL is an MEW class I restricted antigen derived from the ovalbumin protein. CPPs covalently linked to SIINFEKL have shown promise in their ability to deliver and induce and immune response. Results shown herein demonstrates efficient non-covalent delivery of SIINFEKL into monocytes in whole blood, as well as immature dendritic cells in vitro for presentation on the MHC class I using the amphiphilic block copolymer PTDM Me-Ph$_{10}$-dG$_5$. Additionally, the differentiation of the monocytes and production of inflammatory cytokines was explored with the co-delivery of endosomal TLR9 agonist CpG. Understanding the efficacy of these PTDMs provides an important foundation for future applications of protein transduction domain technology in the field of polymer and peptide-based vaccines towards intracellular pathogens and immunomodulation of disease.

In one aspect, the invention generally relates to a complex of a peptide with one or more polymer molecules, wherein the peptide is non-covalently complexed to one or more molecules of a block copolymer having the Formula of (I):

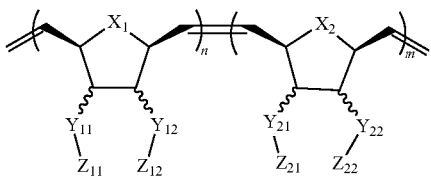

wherein
$X_1$, $X_2$ each is independently O or CH$_2$;
$Y_{11}$, $Y_{12}$ each is independently a single bond or a linking group;
$Z_{11}$, $Z_{12}$ each is independently

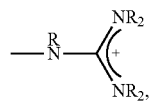

wherein each R is independently hydrogen or a C$_1$-C$_6$ (e.g., C$_1$, C$_2$, C$_3$, C$_4$, C$_5$, C$_6$) alkyl group;
$Y_{21}$, $Y_{22}$ each is independently a single bond or a linking group;
$Z_{21}$, $Z_{22}$ each is independently alkyl, substituted alkyl, aryl, or substituted aryl group;
and
m, n each is independently an integer from about 2 to about 50.

In certain embodiments, each of m and n is independently an integer from about 2 to about 50, for example from about 4 to about 24, from about 6 to about 20, from about 8 to about 16 (e.g., 2, 3, 4, 5, 6, 7, 8, 9, 10, 11, 12, 13, 14, 15, 16, 17, 18, 19, 20, 21, 22, 23, 24). In certain embodiments, one or both m and n is 25 or greater, 30 or greater, or 40 or greater.

In certain embodiments, the peptide comprises about 3 to about 50 (e.g., bout 5 to about 40, from about 6 to about 30, from about 7 to about 20) amino acid residues.

In certain embodiments, the peptide is an antigen. In certain embodiments, the peptide is SIINFEKL.

In certain embodiments, the complex further comprises an agonist complexed to the one or more molecules of a block copolymer. In certain embodiments, the agonist is a TLR9 agonist. In certain embodiments, the agonist is CpG.

In certain embodiments, each of $X_1$ and $X_2$ is O.

In certain embodiments, each of $Y_{11}$, $Y_{12}$, $Y_{21}$ and $Y_{22}$ comprises a carboxylic acid ester, —C(=O)—O—, group.

In certain embodiments, each R is H.

In certain embodiments, at least one of $Z_{21}$ and $Z_{22}$ is an aryl group. In certain embodiments, each of $X_1$ and $X_2$ is O; each of $Y_{11}$, $Y_{12}$, $Y_{21}$ and $Y_{22}$ is a carboxylic acid ester, —C(=O)—O—, group; each R is H; and one of $Z_{21}$ and $Z_{22}$ is methyl and the other is phenyl or benzyl.

In certain embodiments, the complex further comprises a fluorescent or radioactive label that is covalently linked to the copolymer. In certain embodiments, the fluorescent or radioactive label is conjugated to a terminal of the copolymer backbone.

In another aspect, the invention generally relates to a composition comprising a complex disclosed herein.

In certain embodiments, the composition comprises a complex of a peptide non-covalently complexed to one or more molecules of a block copolymer. In certain embodiments, the composition comprises a complex of an antigen and an agonist, each is non-covalently complexed to one or more molecules of a block copolymer.

In yet another aspect, the invention generally relates to a method for delivering a peptide to cytosol. The method comprises: providing a complex of the peptide with a block copolymer; and contacting the complex with a cell under conditions suitable for intracellular uptake of the complex, wherein the block copolymer has the Formula of (I):

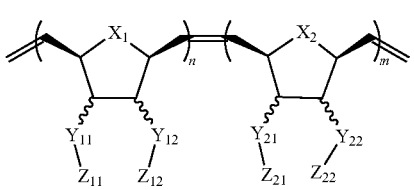

wherein
$X_1$, $X_2$ each is independently O or CH$_2$;
$Y_{11}$, $Y_{12}$ each is independently a single bond or a linking group;
$Z_{11}$, $Z_{12}$ each is independently

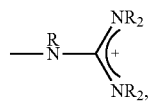

wherein each R is independently hydrogen or a C$_1$-C$_6$ (e.g., C$_1$, C$_2$, C$_3$, C$_4$, C$_5$, C$_6$) alkyl group;

$Y_{21}$, $Y_{22}$ each is independently a single bond or a linking group;

$Z_{21}$, $Z_{22}$ each is independently alkyl, substituted alkyl, aryl, or substituted aryl group; and m, n each is independently an integer from about 2 to about 50.

In yet another aspect, the invention generally relates to a method for concomitant delivery of an antigen and an agonist to cytosol. The method comprises: providing a complex comprising the antigen and the agonist each non-covalently complexed to a block copolymer; and contacting the complex with a cell under conditions suitable for intracellular uptake of the complex, wherein the block copolymer has the Formula of (I):

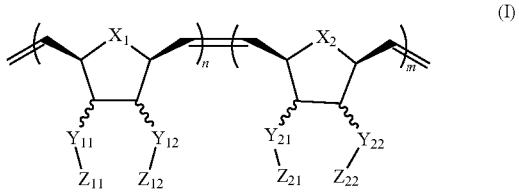

(I)

wherein $X_1$, $X_2$ each is independently O or $CH_2$;

$Y_{11}$, $Y_{12}$ each is independently a single bond or a linking group;

$Z_{11}$, $Z_{12}$ each is independently

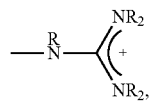

wherein each R is independently hydrogen or a $C_1$-$C_6$ alkyl group;

$Y_{21}$, $Y_{22}$ each is independently a single bond or a linking group;

$Z_{21}$, $Z_{22}$ each is independently alkyl, substituted alkyl, aryl, or substituted aryl group; and m, n each is independently an integer from about 2 to about 50.

In certain embodiments, each of m and n is independently an integer from about 2 to about 50, for example from about 4 to about 24, from about 6 to about 20, from about 8 to about 16 (e.g., 2, 3, 4, 5, 6, 7, 8, 9, 10, 11, 12, 13, 14, 15, 16, 17, 18, 19, 20, 21, 22, 23, 24). In certain embodiments, one or both m and n is 25 or greater, 30 or greater, or 40 or greater.

In certain embodiments, the complex further comprises an agonist complexed to the one or more molecules of a block copolymer.

In certain embodiments, the complex further comprises an agonist complexed to the one or more molecules of a block copolymer. In certain embodiments, the agonist is a TLR9 agonist. In certain embodiments, the agonist is CpG.

In certain embodiments, each of $X_1$ and $X_2$ is O.

In certain embodiments, each of $Y_{11}$, $Y_{12}$, $Y_{21}$ and $Y_{22}$ comprises a carboxylic acid ester, —C(=O)—O—, group.

In certain embodiments, each R is H.

In certain embodiments, at least one of $Z_{21}$ and $Z_{22}$ is an aryl group.

In certain embodiments, each of $X_1$ and $X_2$ is O; each of $Y_{11}$, $Y_{12}$, $Y_{21}$ and $Y_{22}$ is a carboxylic acid ester, —C(=O)—O—, group; each R is H; and one of $Z_{21}$ and $Z_{22}$ is methyl and the other is phenyl or benzyl.

In certain embodiments, the copolymer further comprises a fluorescent or radioactive label covalently linked to the copolymer.

Compositions and methods disclosed herein may be utilized to deliver molecular cargo to the cytosol of various types of cells. In certain embodiments, the delivery is to the cytosol of a leukocyte. In certain embodiments, the delivery is to the cytosol of a monocyte. In certain embodiments, the delivery is to the cytosol of an antigen presenting cell. In certain embodiments, the delivery is to the cytosol of a dendritic cell.

Thus, disclosed herein is an efficient and specific peptide delivery strategy useful, for example, for delivery into monocytes in whole blood, in a rapid process without being innately immunogenic even at increased concentrations lending the ability to tune activation (e.g., using the TLR9 agonist CpG as demonstrated herein). Additionally, the copolymer described here is superior at directing monocyte uptake of the non-covalently complexed cargo when compared with the CPP counterparts that inspired its design.

When SIINFEKL was delivered in combination with CpG in whole blood, a pro dendritic cell cytokine environment was observed signifying the differentiation of the monocytes into professional APCs. Although no inflammatory cytokines were produced in a single culture of THP-1 cells and derived dendritic cells, there was upregulation of CD40, CD80, and CD86 suggesting that further time points as well as concentrations may elucidate monocytes differentiation. Likewise, delivery of both peptide and protein antigen into BMDCs showed uptake and high presentation levels of SIINFEKL in samples treated with the PTDM-SIINFEKL-CpG complexes indicating cytosolic availability.

The enhanced display of SIINFEKL in MEW class I is a promising step toward using PTDMs to stimulate a specific immune response using antigen presenting cells. This study opens the door for further investigation of using amphiphilic polymers to promote antigen and agonist delivery into APCs for training and eliciting a specified activation and response from CTLs.

EXAMPLES

The Examples below describe certain exemplary embodiments of compounds prepared according to the disclosed invention. It will be appreciated that the following general methods, and other methods known to one of ordinary skill in the art, can be applied to compounds and subclasses and species thereof, as disclosed herein.

Delivering peptides and proteins with intracellular function represents a promising avenue for therapeutics, but remains a challenge due to the selective permeability of the plasma membrane. The successful delivery of cytosolically active proteins would enable many opportunities, including improved vaccine development through MEW class I antigen display. Extended research using cell penetrating peptides (CPPs) has aimed to facilitate intracellular delivery of exogenous proteins with some success. A new class of polymer-based mimics termed protein transduction domain mimics (PTDMs), which maintain the positive charge and amphiphilic nature displayed by many CPPs, was developed using a poly-norbornene based backbone. Herein, a previously characterized PTDM was used to investigate delivery of the model antigen SIINFEKL into leukocytes. Peptide delivery into over 90% of CD14+ monocytes was detected in less than 15 minutes with nominal inflammatory cytokine response and high cell viability. The co-delivery of a TLR9 agonist, and antigen using the PTDM into antigen presenting cells in vitro showed presentation of SIINFEKL in association with MEW class I molecules, in addition to upregulation of classical differentiation markers revealing the ability of the PTDM to successfully deliver cargo intracellularly and show application in the field of immunotherapy.

PTDM Design

Norbornene based PTDMs have shown protein delivery including EGFP and Cre into a variety of cell types. An amphiphilic PTDM was chosen that is composed of a hydrophobic block containing one phenylalanine-like side group per monomer and is ten units long connected to a five-unit cationic block that has two arginine-like pendants. To resemble the structure, the polymer is named Me-Ph$_{10}$-b-dG$_5$, where MePh stands for Methyl-Phenyl, and dG corresponds to di-guanidine. The ratio of these two blocks was determined by NMR; their molecular weight and polydispersity (Đ=1.1) were determined by GPC. Additionally, the polymer was also synthesized and terminated with a di-ester group for the addition of a FITC label. (Sgolastra, et al. *J. Control. Release* 2017, 254, 131-136; Madkour, et al. *Macromolecules* 2010, 43, 4557-4561; Backlund, et al. *Biochim. Biophys. Acta-Biomembr.* 2016, 1858 (7); Sgolastra, et al. *Biomacromolecules* 2014, 15 (3), 812-820.)

PTDM Treatment of Whole blood

To understand the interaction of the PTDM with cells in whole blood, FITC labeled PTDM (FIG. 1A) was added to freshly collected human whole blood for 1 hour at a final concentration of 2.8 µM. After lysis of red blood cells (RBCs) and staining with α-CD14 and α-CD15, polymer showed low association with granulocytes (CD15+) and lymphocytes (morphological gate), as seen in FIG. 1C, while the MFI and uptake in monocytes (CD14+) was statistically higher than the blank and the other two cell populations. Viability, determined by staining with 7-AAD, was not statistically different from the blank with 95.8±1.6% live CD14+ monocytes.

Specific uptake by the monocyte population may be attributed to their phagocytotic nature. To probe functional delivery the peptide SIINFEKL was chosen as a model antigen. This peptide is the MHC class I specific sequence of ovalbumin (OVA).

Time Survey of Peptide Delivery into Whole Blood

Figure 2:
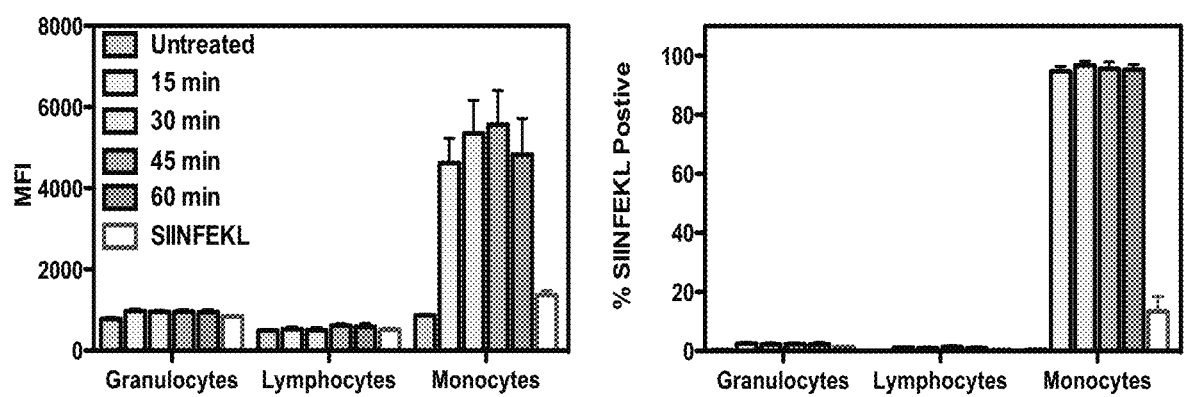
FIG. 2. Delivery of fluorescently labeled SIINFEKL complexed with PTDM at a molar ratio of 1:10 into whole blood for 15, 30, 45, and 60 minutes. Whole blood was also treated with soluble SIINFEKL for 60 minutes as a comparison. Cell types were gated on morphologically then with α-CD14 and α-CD15 to determine true monocytes and macrophages, respectively. The mean±SEM of 4 separate donors is displayed for the 1MFI (left) and % positive (MFI) cells within the established gates.

The specificity of the polymer-antigen complex uptake by monocytes was tested in whole blood. FAM (Fluorescein Amidites) labeled SIIFNEKL was delivered into whole blood using Me-Ph$_{10}$-b-dG$_5$ at a molar ratio of 1:10, for 15, 30, 45, or 60 minutes to investigate the kinetics of uptake. MFI and uptake in monocytes were not statistically different regardless of the incubation time. Additionally, complex uptake was compared with free SIINFEKL-FAM allowed to incubate with whole blood for 60 minutes. High association of the complex with the monocytes is seen within the first 15 minutes (FIG. 2) compared with lymphocytes and granulocytes, consistent with the previous observations. The free peptide is not readily taken up by any leukocytes.

Rapid, specific uptake of the fluorescently labeled antigen in monocytes showcases the ability of the PTDM to significantly enhance uptake of the model cargo. The relatively low association and uptake seen with the free peptide supports the hypothesis that PTDMs facilitate cargo internalization with monocytes. Since the PTDM has been shown to deliver into multiple cell types, increased concentrations were investigated for induced uptake leukocytes populations.

Concentration Survey of Peptide Delivery into Whole Blood

Figure 3:
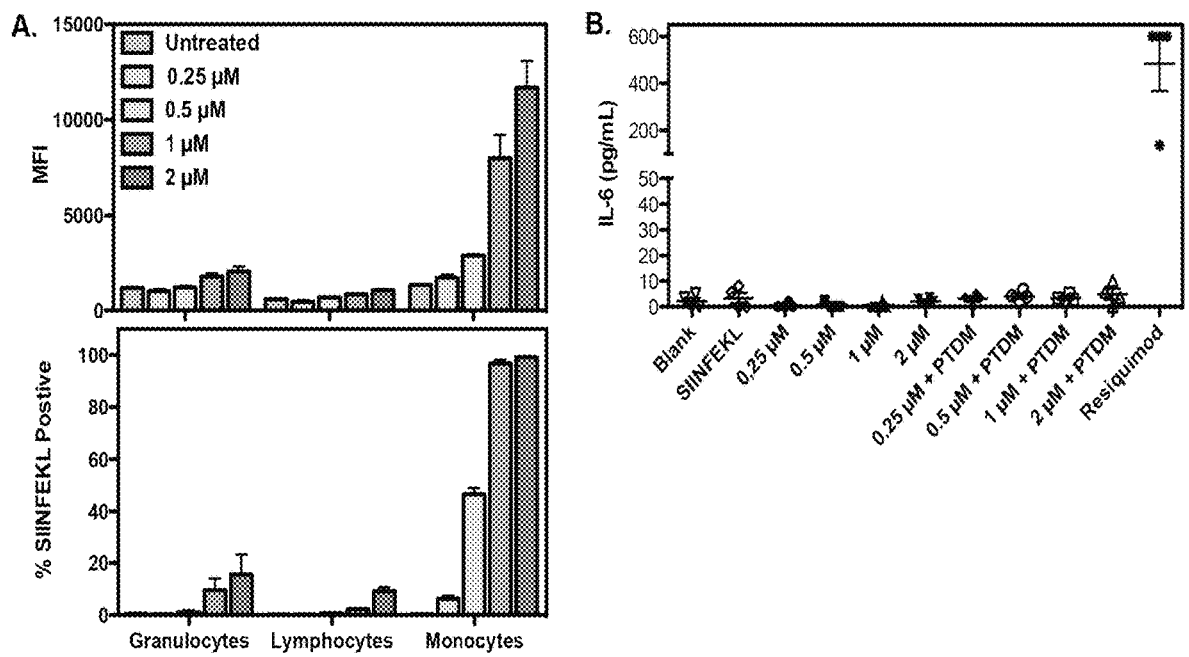
FIG. 3. (A) Delivery of fluorescently labeled SIINFEKL complexed with PTDM at a molar ratio of 1:10 into whole blood at peptide concentrations of 0.25, 0.5, 1, and 2 μM of peptide. Cell types were gated on morphologically then with α-CD14 and α-CD15 to determine true monocytes and macrophages, respectively. (B) IL-6 production was determined for unlabeled SIINFEKL delivered under the same conditions 24 hours after treatment in comparison to the positive control Resiquimod, a TLR7 agonist. The mean±SEM of 4 separate donors is displayed.

FAM labeled SIINFEKL was delivered into whole blood using Me-Ph$_{10}$-b-dG$_5$ at a molar ratio of 1:10 at increasing peptide concentrations (0.25, 0.5, 1, and 2 µM). The MFI and % positive cells are shown in FIG. 3A, suggesting that 1 µM of peptide was optimal because monocytes show almost complete uptake and the MFI is significantly distinguishable from the untreated sample. Increasing the concentration to 2 µM appears to yield a higher MFI but does not increase the number of cells with the cargo. High uptake was exhibited almost exclusively in the monocytes labeled with CD14 and not significantly in the lymphocytes and granulocytes, consistent with the previous observations.

Even at high concentrations, antigen uptake is seen almost exclusively in the monocyte population, confirming that the polymer promotes specific interactions with these phagocytic cells. Monocytes can differentiate into two types of professional APCs, macrophages and dendritic cells, upon stimulation and activation. Usually, the differentiation into dendritic cells can be marked by a change in cell specific surface marker expression such as upregulation of MHC class I and DC-sign (CD209) as well as increase inflammatory cytokine production. (van Helden, et al. *Immunol. Lett.* 2008, 117 (2), 191-197; Murphy, et al. *Janeway's Immunobiology*, 8th ed.; Garland Science, Taylor & Franscis Group LLC: New York, 2012; Daigneault, et al. *PLoS One* 2010, 5 (1), e8668.)

To further investigate the ability of the polymer-peptide complexes to cause an inflammatory cytokine environment, whole blood was treated with the same conditions as in the concentration survey (0.25, 0.5, 1, and 2 µM peptide at a 1:10 molar ratio of peptide to polymer) and the production of IL-6 was probed 24 hours after treatment (FIG. 3B). The whole blood was added to the polymer complexes for 1 hour on rotation, after which the plasma was removed and the cells were washed three times with non-supplemented RPMI. The cells were incubated at 37° C. for an additional 24 hours and the supernatant was collected to perform an IL-6 ELISA. No significant IL-6 production was detected with any of the treatments, except the positive control Resiquimod, a TLR7/8 agonist. The results indicate the polymers alone and in complex with SIINFEKL do not produce pro-inflammatory signals in blood, even at high concentrations. Since the complexes show high uptake but are not inflammatory, they most likely do not cause the monocytes to differentiate allowing differentiation and activation of the monocytes to be induced by delivering an agonist.

SIINEKL Delivery with Amphiphilic Peptides

R9 and Pep-1, two commonly cited CPPs, were tested alongside Me-Ph$_{10}$-b-dG$_5$ to compare their ability to non-covalently facilitate SIINFEKL uptake in whole blood. While R9 is strictly cationic and pep-1 is designed to be amphiphilic, both peptides have previously demonstrated ability to noncovalently deliver cargos into cells. Similar to the PTDM, the two peptides (R9 and Pep-1) were complexed for 30 minutes in the presence of SIINFEKL. Since delivery in the presence of protein inhibits the ability of many carriers to deliver into cells, plasma was removed from the blood by washing with RPMI three times and suspending the cells back to the original collected volume. The plasma free blood was then added to the complexes and put on rotation for 1 hour at 37° C. after which the RBCs were lysed and cells were stained with α-CD14. (Morris, et al. *Nat. Biotechnol.* 2001, 19 (December), 1173-1176; Nakamura, et al. *Mol. Pharm.* 2014, 11 (8), 2787-2795; Chang, et al. *Curr. Pharm. Biotechnol.* 2014, 15 (3), 267-275.)

Figure 4:
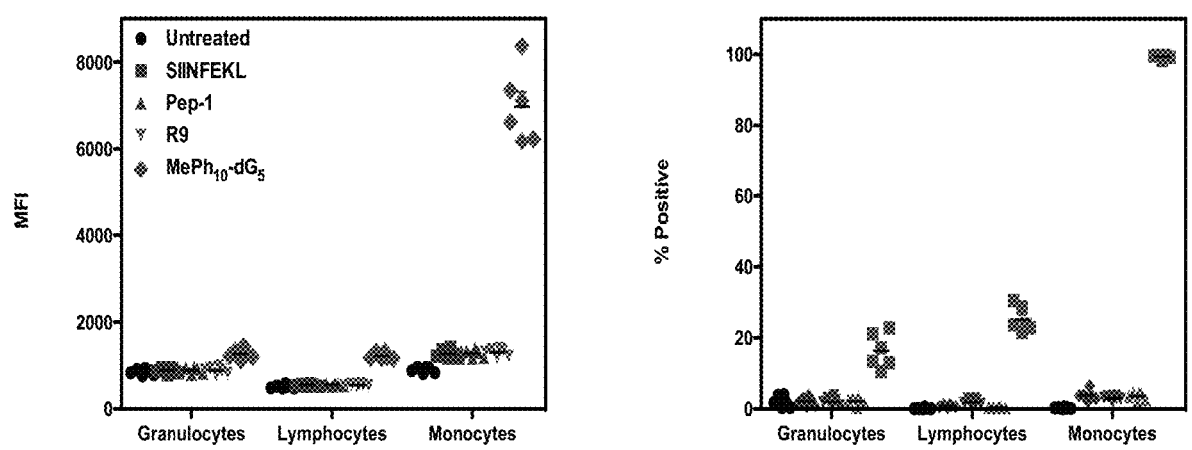
FIG. 4. Delivery of fluorescently labeled SIINFEKL into whole blood using the well-known cell penetrating peptides pep-1 and R9 in comparison with MePh₁₀-b-dG₅ after 1 hour incubation. Cell types were gated on morphologically then FIG. 5. Delivery of SIINFEKL-FAM (A) and OVA-AF647 (B) into THP-1 cells using Me-Ph$_{10}$-b-dG$_5$. Cells were treated for 4 hours, then washed 3 times with heparin (20 U/mL) and assessed for uptake of the cargos by flow cytometry. Upregulation of activation surface markers (C) on THP-1s 24 hours after delivery of polymer-antigen-agonist complexes. Cells were treated for 4 hours, then washed one time with media and allowed to incubate for 20 more hours. LPS was used as a positive control. Cells were stained with antibodies for DC-sign (CD209), HLA-DR (MHC II), CD86, CD80, and CD40. The mean±SEM are shown from 3 independent experiments.

Analysis by flow cytometry, shown in FIG. 4, indicated negligible delivery when the SIINFEKL was introduced by itself or non-covalently complexed with peptides R9 and Pep-1. In contrast, the PTDM facilitated uptake in the monocytes. This data, in the absence of plasma proteins, also demonstrates that plasma proteins coating the PTDM-SIINFEKL complex are not responsible for the uptake of the polymer-antigen complex in terms of aggregation or opsonization.

Cytokine Response to Co-Delivery of SIINFEKL and CpG in Whole Blood

A multi-analyte inflammatory cytokine panel was used to understand the immune response when CpG was added to the complexes. GpC, a nonfunctional analogue of CpG, was included as a negative control to preclude the role of nonspecific TLR9 activation during incubation. At 24 hours, following the 60-minute treatment with the non-covalent polymer-SIINFEKL-CpG complexes, supernatants from whole blood were tested the inflammatory cytokines: IL-1β, IFN-α, IFN-γ, TNF-α, MCP-1, IL-6, IL-8, IL-10, IL-12p70, IL-17A, IL-18, IL-23, and IL-33. A statistical summary of cytokine production is shown in Table 1, where statistical significance from the control sample is denoted by shading. SIINFEKL is not immunogenic to humans and showed no increase in inflammatory response as expected. The TLR9 agonist CpG does cause a significant production of IL-6 and MCP-1, which are consistent with general inflammation and activation of monocytes respectively. When CpG was delivered using the PTDM, it caused an increase in IL-1β, IFN-α, TNF-α, and IL-12p70, in addition to IL-6, MCP-1, which are all indicative of a pro-inflammatory response directed by the differentiation and activation of professional APCs. In general, cytokine response with the addition of SIINFEKL to the PTDM and CpG did not change this profile, suggesting that the two cargos can be delivered together to perform their individual functions. Notably, the polymer by itself and delivering SIINFEKL did not induce the production of inflammatory cytokines, suggesting that the amount of agonist could be tailored regulate an appropriate reaction toward the peptide vaccine.

Figure 5:
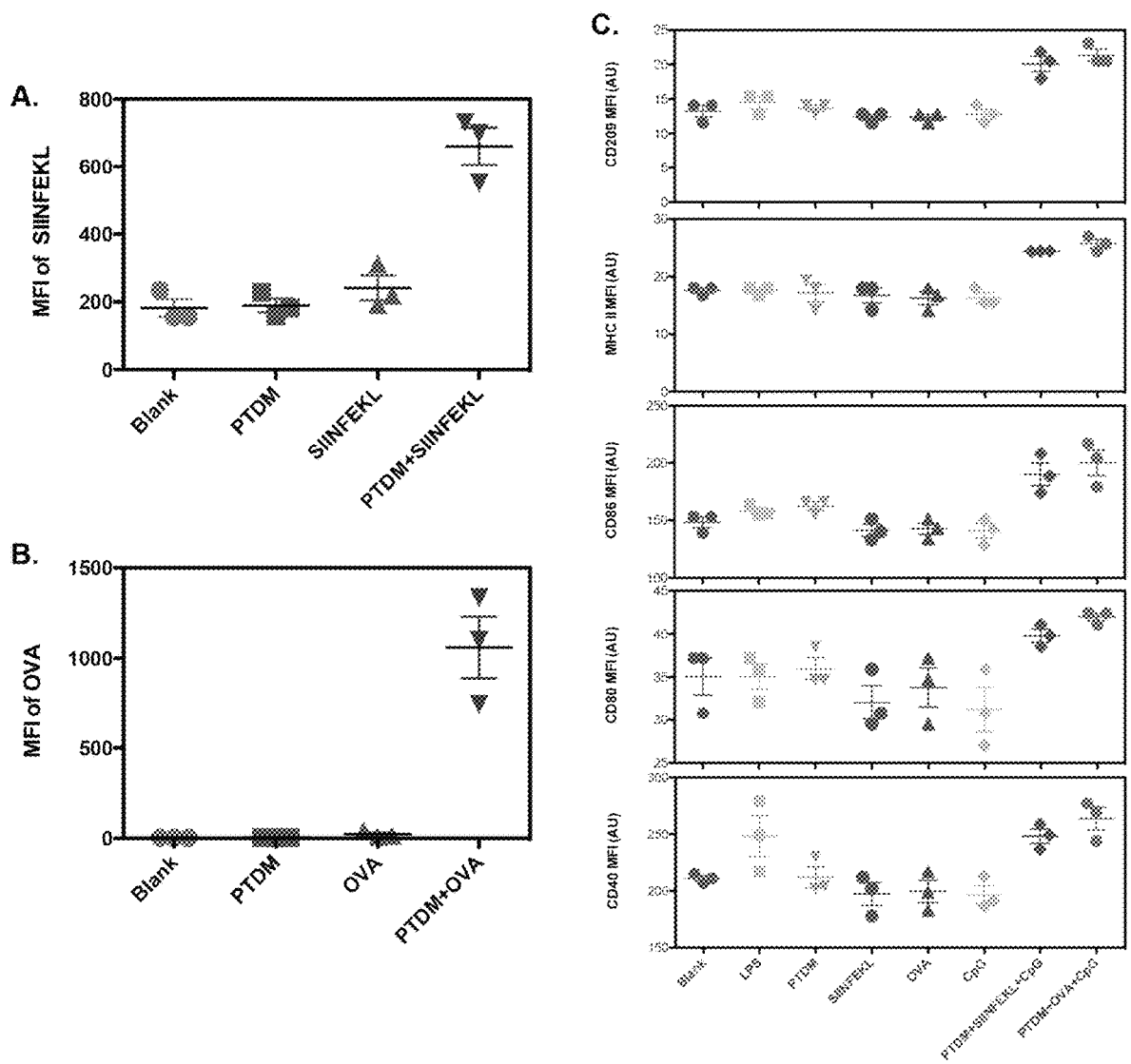

FIG. 5A-5B, confirming its ability to deliver into this cell type. Viability, determined by 7-AAD staining, remained similar to untreated cells above 95% in relation to the untreated blank.

To understand the differentiation and activation of the monocytes by PTDM-antigen-agonist complexes, the 10 μM Me-Ph$_{10}$-b-dG$_5$ was complexed with 1 μM unlabeled SIINFEKL or OVA along with 1 μM CpG for 30 minutes and cells were treated for four hours. The cells were washed before being suspended in complete media for an additional 20 hours, after which the supernatant was collected for ELISA and the cells were stained with antibodies for the activation markers CD11c, CD40, CD80, CD86, and MEW class II (HLA-DR). Minor upregulation of all of the tested markers was seen in samples treated with the PTDM-antigen-agonist complex (FIG. 5C) compared with treatment with of either the antigen or agonist alone. The display of these classical activation markers is consistent with differentiation of monocytes into monocyte derived dendritic cells. In combination with its ability to facilitate high levels of antigen presentation in MHC class I, the co-delivery of CpG into the cells causes upregulation of important co-stimulatory molecules that are necessary for enhancing a CD8+ T cell response. While neither the antigen or agonist alone is able to phenotypically change the THP-1, using the PDTM to deliver both cargos has potential to activate and differentiate monocytes into their APC counterparts.

Delivery into Bone Marrow Derived Dendritic Cells

Perhaps the most conventional and telling way to scrutinize whether the PTDM-antigen-agonist complex will enhance vaccination through delivery of a specific peptide is to probe immature dendritic cells that would subsequently be able to stimulate T cells. In this case, complexes are delivered into mouse bone marrow derived dendritic cells (BMDCs) that would internally process the antigen via the MHC class I and class II pathways and present the antigen along with respective costimulatory molecules. Since a peptide that is specifically presented in MHC class I is chosen, the display, as well as the upregulation of CD86, a costimulatory molecule can be probed.

TABLE 1

Inflammatory cytokine panel for the co-delivery of SIINFEKL and CpG using MePh$_{10}$-b-dG$_5$ into whole blood*

|  | IL-1B | IFN-a | IFN-g | TNF-a | MCP-1 | IL-6 | IL-12p70 | IL-8 | IL-10 | IL-17A | IL-23 | IL-33 |
|---|---|---|---|---|---|---|---|---|---|---|---|---|
| SIINFEKL | 1.0 | 1.0 | 0.7 | 1.0 | 1.4 | 1.0 | 1.0 | 1.1 | 1.0 | 0.6 | 0.8 | 1.0 |
| CpG | 1.0 | 2.7 | 0.9 | 1.0 | 3.6*** | 1.4*** | 1.0 | 0.8 | 1.0 | 0.7 | 0.9 | 1.0 |
| GpC | 1.2 | 1.0 | 1.3 | 1.0 | 1.3 | 1.0 | 1.0 | 1.1 | 1.0 | 1.3 | 1.0 | 1.0 |
| SIINFEKL + CpG | 1.2 | 3.8 | 1.6 | 1.0 | 4.1*** | 1.5*** | 1.1 | 0.8 | 1.0 | 1.3 | 1.1 | 1.0 |
| PTDM | 1.1 | 1.0 | 1.4 | 1.0 | 1.5 | 1.0 | 1.0 | 1.5 | 1.0 | 1.3 | 1.0 | 1.0 |
| PTDM + SIINFEKL | 1.3 | 1.0 | 1.9 | 1.1 | 1.2 | 1.1 | 1.1 | 1.1 | 1.1 | 1.8 | 1.3 | 1.0 |
| PTDM + CpG | 1.4** | 34.3*** | 2.0 | 1.3** | 5.1*** | 1.4** | 1.5*** | 0.9 | 1.1 | 1.9 | 1.5 | 1.1 |
| PTDM + SIINFEKL + CpG | 1.3 | 38.3*** | 1.5 | 1.2 | 4.8*** | 1.4** | 1.5*** | 0.8 | 1.0 | 1.4 | 1.2 | 1.1* |
| IL-4 + GM-CSF | 1.0 | 1.2 | 0.7 | 1.0 | 4.7*** | 1.1 | 1.0 | 2.8*** | 1.0 | 0.8 | 0.9 | 1.0 |
| DMSO | 1.2 | 1.0 | 1.3 | 1.0 | 1.0 | 1.0 | 1.0 | 1.3 | 1.0 | 1.2 | 1.1 | 1.0 |

*Supernatant was collected 24 hours after treatment and analyzed using a cytometric bead array. Plotted values are the fold change compared to untreated sample and statistical difference was determined compared with the untreated sample from 3 independent donors (*p < 0.05, p < 0.005, *p < 0.0005)

Delivery into THP-1 Monocytes

Figure 6:
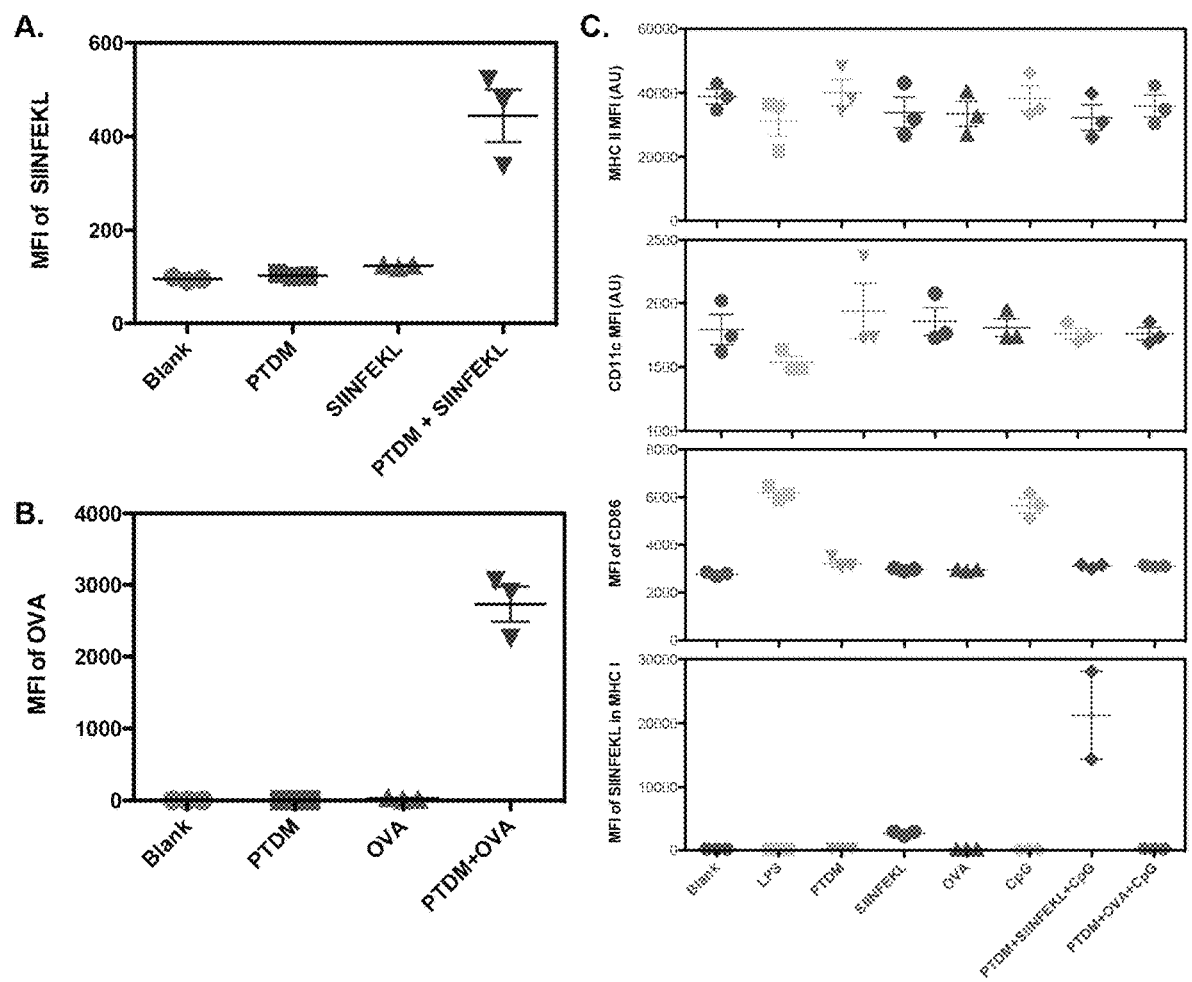
FIG. 6. Delivery of SIINFEKL-FAM (A) and OVA-AF647 (B) using Me-Ph$_{10}$-b-dG$_5$ into immature dendritic cells derived from C57BL/6 mouse bone marrow. Cells were treated for 4 hours, then washed 3 times with heparin (20 U/mL) and assessed for uptake of the cargos by flow cytometry. Upregulation of activation markers (C) on BMDCs 24 hours after delivery of polymer-antigen-agonist complexes. Cells were treated for 4 hours, then washed one time with media and allowed to incubate for 20 more hours. LPS was used as a positive control. Cells were stained with antibodies for MHC II, CD11c, CD86, and H-2K$^b$ (presentation of SIINFEKL in MHC class I). The mean and SEM are shown for BMDCs derived from 3 mice.

FAM labeled SIINFEKL or OVA labeled with FITC were delivered respectively using Me-Ph$_{10}$-b-dG$_5$ into THP-1s, a human monocyte cell line. 1 μM of each cargo was complexed respectively with the polymer at a 1:10 protein/peptide to polymer molar ratio for 30 minutes before application to cells in complete media. Cells were treated for 4 hours, then washed 3 times with 20 U/mL heparin prior to analysis by flow cytometry. The Me-Ph$_{10}$-b-dG$_5$ facilitated delivery of both cargos into the THP-1 monocytes, shown in To test SIINFEKL delivery and presentation for T cell activation, bone marrow derived dendritic cells were differentiated from B56 mouse bone marrow for 6 days in the presence of 20 ng/mL mouse GM-CSF. After 6 days, cells were harvested and treated with 1 μM fluorescently labeled SIINFEKL or OVA both free and in complex with PTDM molar ratio of 1:10 for 4 hours. Substantial uptake was seen in the presence of polymers while significantly less uptake was seen for the free antigen in both cases (FIG. 6A-6B).

In addition to delivery of fluorescently labeled cargo, both OVA and SIINFEKL were delivered in combination with 1 µM CpG to investigate presentation of SIINFEKL in the MHC class I along with upregulation of CD86 and the production of inflammatory cytokines indicating the ability of these DCs to activate T cells. After differentiation, cells were treated for 4 hours with the polymer-antigen-agonist complexes, after which cells were washed 1 time with PBS and suspended in fresh media for 20 hours. To determine upregulation, cells were stained with antibodies for CD11c and WIC class II to indicate DCs, as well as CD86, and H-$2K^b$ and results are shown in FIG. 6C.

Since SIINFEKL can be extracellularly loaded into the MHC class I by diffusion,[33] some display was expected just by adding the soluble peptide to the cells. The presentation of SIINFEKL on the MHC class I was observed to be significantly higher for samples treated with polymer-SIINFEKL-CpG compared with just soluble SIINFEKL alone or when the polymer is used to deliver only the peptide. The high level of the antigen in the MHC class I confirms that the complexes deliver and facilitate presentation for T cell stimulation. Unexpectedly, the costimulatory molecule CD86 was not significantly upregulated in any of the polymer treated samples, though the time point or concentration of chosen agonist may directly affect display of this marker.

Additionally, samples treated with polymer-OVA-CpG did not result in any display of SIINFEKL on the MHC class I as determined by staining with the H-$2K^b$. Lack of display for OVA treated samples may be due to slow and inconsistent processing of the OVA protein intracellularly. Higher presentation may be observed at a different time point or at higher concentrations of OVA. While delivering a complete protein is conceptually interesting, the ability to deliver a specific sequence or set of sequences allows more control over what the specific immune response will be against.

Experimental
PTDM Synthesis and Characterization

Monomers and polymers were synthesized according to previously established procedures.[27,28] To create the monomer, the exo Diels-Alder adduct of maleic anhydride and furan was ring-opened with the desired alcohol to introduce the first substituent. A second alcohol was then added using EDC coupling. The desired polymers were obtained by ring-opening metathesis polymerization using Grubb's third generation catalyst in dichloromethane and end terminated with either ethyl vinyl ether or an activated ester, which was then reacted with FITC. After polymerization, the Boc groups protecting the guanidinium groups were removed with a 1:1 solution of trifluoroacetic acid and dichloromethane. The final products were purified by dialysis against RO water and recovered by lyophilization. The resulting Me-$Ph_{10}$-$dG_5$ was characterized for size distribution by gel permeation chromatography resulting in a PDI of 1.1 and by end group analysis by nuclear magnetic resonance to determine the ratio of blocks. (Backlund, et al. *Biochim. Biophys. Acta*—Biomembr. 2016, 1858 (7).)

Cell Preparation and Culture
Whole Blood

Whole human blood was obtained from healthy volunteers under signed consent in Roche Vacutainers containing hirudin. In all cases, blood was used within 10 minutes of the tapping from the donor. The blood was distributed into Eppendorf tubes containing preassembled polymer preparations in RPMI 1640 with no supplements and incubated up to 1 hour at 37° C. on rotation (60 RPM). In general, 400 µL of blood was combined with 100 µL of polymer complex prepared in RPMI 1640 for a final volume of 500 µL.

In the case of plasma free whole blood delivery, whole blood was centrifuged at 200 g immediately upon receipt, plasma was removed, and cells were washed with RPMI 1640 three times before suspension to the original volume with RPMI 1640. The washed blood was then allocated to the polymer preparations and incubated on rotation (60 RPM) for 1 hour at 37° C.

Cell Lines

THP-1 cells (ATCC TIB-202), were grown in RPMI 1640 supplemented with 10% (v/v) FBS, L-glutamine, Non-Essential Amino Acids (NEAA), Na-pyruvate, HEPES, 100 U/mL penicillin, and 100 U/mL streptomycin at 37° C., 5% $CO_2$ and were passaged 24 hours before treatment. Polymers were mixed with cargo and allowed to complex for 30 minutes. Cells were harvested and suspended in fresh complete media and placed into a 12 well plate at $4\times10^5$ cells/mL. Polymer-cargo complexes were applied drop-wise to each well. Cells were treated for 4 hours, then washed 3 times with 20 U/mL heparin in PBS before being suspended in 0.2% BSA in PBS FACS buffer and stained with 7-AAD for analysis by flow cytometry.

To establish immature dendritic cells, previously established protocols were used. (van Helden, et al. *Immunol. Lett.* 2008, 117 (2), 191-197.) Briefly, THP-1s were incubated with 100 ng/mL IL-4 and 100 ng/mL GM-CSF for 5 days, with the media and cytokines being replaced every 2 days. Differentiation was confirmed by increased expression in CD11c and HLA-DR as well as a morphological change.

Bone Marrow Derived Dendritic Cells

Immature dendritic cells were differentiated from murine bone marrow according to established protocols. (Dewitte, et al. *J. Control. Release* 2014, 195, 138-146.) RBCs were lysed using BioLegend® lysis buffer and cells were plated at a density of $2\times10^5$ cells/mL in complete RPMI (listed under cell lines) with the addition of 20 ng/mL recombinant mouse GM-CSF. Cells were cultured for 6 days with the addition of 10 mL fresh media and cytokines on day 3. Non-adherent and loosely adherent cells were harvested on day 6 and cells were pelleted, counted, and plated at a density of $2\times10^6$ cells/mL.

Flow Cytometry

After incubation, cells were pelleted at 200 g for 5 minutes and the supernatant was removed. Red blood cells were lysed in using BD Pharm lysis buffer and subsequently washed with 1% FBS in PBS twice before staining with antibodies. Unspecific binding was blocked for 10 minutes using human or mouse IgG respectively. Antibody surface staining was performed using Human CD14-APC, CD40-PE, CD80-AF488, CD86-BV711, CD209-APC, HLA-DR-APC-Cy7, or mouse CD11c-AF488, CD86-AF647, HLA-DR, H-$2K^b$-PE as indicated by manufacturer (BD® or BioLegend®).

Briefly, cells were transferred to a 96 well plate where the respective antibodies were added accordingly. Samples were incubated for 30 minutes on ice after which samples were washed 3 times with 1% FBS in PBS before analysis by flow cytometry.

Whole blood samples were collected on a BD Accuri C6 flow cytometer with two lasers (488 and 640nm) with three channels on the blue laser (533/30, 585/40, and 670 LP) and one channel on the red laser (675/25). For whole blood experiments, 100,000 single events were collected for each sample using a minimum FSC-H cutoff of 1,200,000. Within the single cell gate, 7AAD positive cells were excluded from analysis.

THP-1 monocytes, immature dendritic cells, and bone marrow derived dendritic cells were analyzed using a BD LSR Fortessa 20X flow cytometer with five lasers and 18 channels. For both cell lines, 10,000 single events were collected for each sample, while for the bone marrow derived cells, a minimum of 50,000 single cell events were collected. Only cells negative for 7-AAD were assessed for either uptake or presentation of markers. Multi-color flow cytometric analysis spectral overlap was corrected by appropriate compensation and analyzed using FlowJo 10.2 (v3.05470) by Tree Star, Ashland, OR, USA.

Cytokine Profiling

After one hour of incubation with treatment as reported under cell preparation and culture, cells were pelleted at 400 g for 2 minutes and supernatant was removed. Cells were washed 3 times with RPMI supplemented with 100 U/mL pen/strep, and plated into a 96 well round bottom plate where they were incubated at 37° C. and 5% $CO_2$ for 24 hours. After incubation, cells were pelleted at 5000 g and supernatant was −80° C. Measurements of IL-6 were performed immediately after thawing frozen supernatant using ELISA, R&D Systems. Cytokine production was detected using the human inflammation cytometric bead array Legendplex™ from BioLegend® (740118).

Statistical Analysis

All flow cytometry experiments were repeated in at least biological triplicate. Data sets were expressed as means ±SEM Statistical significance of differences was determined by one- or two-way ANOVA followed by a Bonferroni post hoc test. Differences were considered statistically significant for $p<0.05$. Statistical analysis was performed using Prism™ 5.0a by Graphpad® Software.

Materials, compositions, and components disclosed herein can be used for, can be used in conjunction with, can be used in preparation for, or are products of the disclosed methods and compositions. It is understood that when combinations, subsets, interactions, groups, etc. of these materials are disclosed that while specific reference of each various individual and collective combinations and permutations of these compounds may not be explicitly disclosed, each is specifically contemplated and described herein. For example, if a method is disclosed and discussed and a number of modifications that can be made to a number of molecules including in the method are discussed, each and every combination and permutation of the method, and the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed compounds or compositions. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

Applicant's disclosure is described herein in preferred embodiments with reference to the figures, in which like numbers represent the same or similar elements. Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

The described features, structures, or characteristics of Applicant's disclosure may be combined in any suitable manner in one or more embodiments. In the description, herein, numerous specific details are recited to provide a thorough understanding of embodiments of the invention. One skilled in the relevant art will recognize, however, that Applicant's composition and/or method may be practiced without one or more of the specific details, or with other methods, components, materials, and so forth. In other instances, well-known structures, materials, or operations are not shown or described in detail to avoid obscuring aspects of the disclosure.

In this specification and the appended claims, the singular forms "a," "an," and "the" include plural reference, unless the context clearly dictates otherwise.

Unless defined otherwise, all technical and scientific terms used herein have the same meaning as commonly understood by one of ordinary skill in the art. Although any methods and materials similar or equivalent to those described herein can also be used in the practice or testing of the present disclosure, the preferred methods and materials are now described. Methods recited herein may be carried out in any order that is logically possible, in addition to a particular order disclosed.

INCORPORATION BY REFERENCE

References and citations to other documents, such as patents, patent applications, patent publications, journals, books, papers, web contents, have been made in this disclosure. All such documents are hereby incorporated herein by reference in their entirety for all purposes. Any material, or portion thereof, that is said to be incorporated by reference herein, but which conflicts with existing definitions, statements, or other disclosure material explicitly set forth herein is only incorporated to the extent that no conflict arises between that incorporated material and the present disclosure material. In the event of a conflict, the conflict is to be resolved in favor of the present disclosure as the preferred disclosure.

EQUIVALENTS

The representative examples are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples and the references to the scientific and patent literature included herein. The examples contain important additional information, exemplification and guidance that can be adapted to the practice of this invention in its various embodiments and equivalents thereof.

The invention claimed is:

1. A complex of a peptide with one or more polymer molecules, wherein the peptide is an antigen comprising about 3 to about 50 amino acid residues and is non-covalently complexed to one or more molecules of a block copolymer having the Formula of (I):

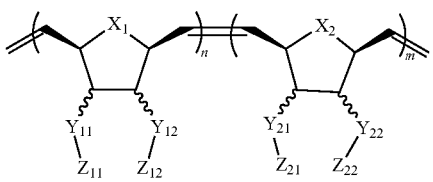
(I)

wherein
$X_1$, $X_2$ each is independently O or $CH_2$;
$Y_{11}$, $Y_{12}$ each is independently a single bond or a linking group;
$Z_{11}$, $Z_{12}$ each is independently

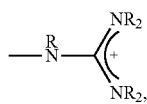

wherein each R is independently hydrogen or a $C_1$-$C_6$ alkyl group;
$Y_{21}$, $Y_{22}$ each is independently a single bond or a linking group;
$Z_{21}$, $Z_{22}$ each is independently alkyl, substituted alkyl, aryl, or substituted aryl group; and m, n each is independently an integer from about 2 to about 50,
wherin the complex further comprises a TLR9 agonist CpG and is non-covalently complexed to the one or more molecules of a block copolymer having the Formula (I).

2. The complex of claim 1, wherein the antigen is SIINFEKL.

3. The complex of claim 1, wherein each of $X_1$ and $X_2$ is O.

4. The complex of claim 1, wherein each of $Y_{11}$, $Y_{12}$, $Y_{21}$ and $Y_{22}$ comprises a carboxylic acid ester, —C(=O)—O—, group.

5. The complex of claim 1, wherein each R is H.

6. The complex of claim 1, wherein at least one of $Z_{21}$ and $Z_{22}$ is an aryl group.

7. The complex of claim 1, wherein
each of $X_1$ and $X_2$ is O;
each of $Y_{11}$, $Y_{12}$, $Y_{21}$ and $Y_{22}$ is a carboxylic acid ester, —C(=O)—O—, group;
each R is H; and
one of $Z_{21}$ and $Z_{22}$ is methyl and the other is phenyl or benzyl.

8. The complex of claim 1, wherein each of m and n is an integer from about 3 to about 25.

9. The complex of claim 1, further comprising a fluorescent or radioactive label covalently linked to the copolymer.

10. A composition comprising a complex of claim 1.

* * * * *